United States Patent
Zimmermann et al.

(10) Patent No.: US 7,317,314 B2
(45) Date of Patent: Jan. 8, 2008

(54) METHOD FOR MEASURING STRESS/STRAIN USING BARKHAUSEN NOISES

(75) Inventors: Werner Zimmermann, Putzbrunn (DE); Juergen Halm, Ganderkesee (DE)

(73) Assignees: EADS Deutschland GmbH, Ottobrunn (DE); AIRBUS Deutschland GmbH, Hamburg (DE)

( * ) Notice: Subject to any disclaimer, the term of this patent is extended or adjusted under 35 U.S.C. 154(b) by 206 days.

(21) Appl. No.: 10/525,077

(22) PCT Filed: Aug. 16, 2003

(86) PCT No.: PCT/EP03/09085

§ 371 (c)(1),
(2), (4) Date: Feb. 18, 2005

(87) PCT Pub. No.: WO2004/018985

PCT Pub. Date: Mar. 4, 2004

(65) Prior Publication Data

US 2005/0248338 A1   Nov. 10, 2005

(30) Foreign Application Priority Data

Aug. 20, 2002 (DE) ................. 102 39 017

(51) Int. Cl.
*G01B 7/24* (2006.01)
*G01L 1/12* (2006.01)

(52) U.S. Cl. ........................ 324/209; 73/779

(58) Field of Classification Search ........... 324/209, 324/228, 234–243; 73/761, 779, 862.69
See application file for complete search history.

(56) References Cited

U.S. PATENT DOCUMENTS

| | | | |
|---|---|---|---|
| 4,279,163 A * | 7/1981 | Takekoshi et al. | 73/761 |
| 4,466,287 A * | 8/1984 | Repplinger et al. | 73/643 |
| 4,596,150 A * | 6/1986 | Kuhr | 73/779 |
| 4,692,701 A * | 9/1987 | Dundas et al. | 324/240 |
| 4,881,030 A | 11/1989 | Stuecker et al. | |
| 4,931,730 A | 6/1990 | Olsen et al. | |
| 4,977,373 A | 12/1990 | Tiitto | |
| 5,164,669 A * | 11/1992 | Namkung et al. | 324/209 |
| 5,166,613 A | 11/1992 | Perry | |
| 5,280,725 A * | 1/1994 | Stengel | 73/761 |

FOREIGN PATENT DOCUMENTS

| | | |
|---|---|---|
| DE | 147 580 | 4/1981 |
| DE | 40 33 494 A1 | 10/1990 |
| DE | 196 31 311 C2 | 8/1996 |
| JP | 11-337527 | 12/1999 |

* cited by examiner

Primary Examiner—Reena Aurora
Assistant Examiner—Kenneth J Whittington
(74) Attorney, Agent, or Firm—Crowell & Moring LLP

(57) ABSTRACT

In a method of measuring stress/strain by detecting Barkhausen noise, an exciting/sensing device is arranged at least adjacent to a magnetic or magnetizable element, and passing an increasing magnetizing current through the exciting device. The start of the Barkhausen noise in the element, as a function of the magnetizing current is detected by the sensing device, and the magnetizing current at that time represents a measurement of the stress/strain condition of the element.

10 Claims, 2 Drawing Sheets

METHOD FOR MEASURING STRESS/STRAIN USING BARKHAUSEN NOISES

BACKGROUND AND SUMMARY OF THE INVENTION

This application claims the priority of German patent document 102 39 017.7, filed Aug. 20, 2002 (PCT International Application No. PCT/EP2003/009085), the disclosure(s) of which is (are) expressly incorporated by reference herein.

The present invention relates to a method of measuring stress/strain by means of Barkhausen noise, such as may be used, for example, to measure stress/strain in bolts or rivets at the wing or fuselage of an airplane, particularly during maintenance work.

For example, for tightening bolts, torque wrenches have been used, while simultaneously determining the internal stress in the bolt by means of ultrasonic measurements. However, this technique requires that the bolt be coated or laminated with a piezoelectric, which makes it considerably more expensive.

In addition, it is known to use micromagnetic methods and sensors which measure Barkhausen noise to detect material changes caused by treatment processes, based on the proposition that the magnetic structure of the materials is influenced by the characteristics of the material. Crystallite limits and other inhomogeneities (such as dislocations, foreign atoms and inclusions) hinder the movement of the so-called Bloch walls; and detachment of the walls from inhomogeneities results in "bounces" in the magnetization, or so-called "Barkhausen noise". These jolt-type movements of the Bloch walls can be recorded in the form of brief electric pulses, using a coil. The number, height and intensity of the pulses depends on the material and its condition.

Such a method for the nondestructive evaluation of ferromagnetic materials is known, for example, from German Patent Document DE 196 31 311 C2. The measuring principle is based on the fact that, when a ferromagnet is periodically reversed, the magnetic domain structure is continuously changed, and boundaries between areas of the same magnetization (that is, Bloch walls) move through the material structure and interact with the microstructure of the material. This interaction is received as an electromagnetic signal—the so-called Barkhausen noise.

Such methods, which are based on an analysis of the Barkhausen noise, are generally used for quality control; for example, for optimizing different treatment processes (grinding, heat treatment, etc.) of components. The components may, for example, be ground parts, camshafts, crankshafts, bearings, gear wheels, injection valves and numerous other parts from automotive engineering and the aerospace field.

One object of the invention is to provide a fast and simple method of measuring stress/strain.

Another object of the invention is to provide such a method which is capable of determining stress/strain conditions in fastening devices.

These and other objects and advantages are achieved by the method according to the invention, in which an exciting/sensing device is arranged at least adjacent to one magnetic or magnetizable element (preferably in a partial area around the magnetic or magnetizable element), so that it is acted upon by a rising magnetizing current. The sensing device thus detects the starting of the Barkhausen noise in the element (which is a measurement of the stress/strain condition of the element) as a function of the magnetizing current. Expediently, the starting of the Barkhausen noise is determined by a comparative measurement relative to reference values.

The invention has the advantage that the physical effect of the Barkhausen noise is effectively utilized. The stress/strain condition of a magnetic or magnetizable element (preferably ferromagnetic) is determined in a contactless manner by a simple mounting of an exciting/sensing device. In this case, the element is magnetized by the magnetic field generated by the exciting device, and the sensing device detects the Barkhausen noise.

In a preferred embodiment, the exciting/sensing device is constructed in one piece (preferably a single coil), which acts simultaneously as an exciting device and a sensing device. The sensing device detects the magnetizing current at which the Barkhausen noise occurs, the magnetizing current being proportional to the internal stress in the element. Such an arrangement has the advantage that the equipment expenditures are kept as low as possible.

In an alternative embodiment, the exciting device is again constructed as a coil, but the sensing device for detecting the Barkhausen noise is an acoustic or interferometric detector, which is notable for its small dimensions.

A pulsed magnetizing current is expediently used for excitation, and during the off-time of the pulses, the sensing device is set to receive the Barkhausen noise. This arrangement has the advantage that higher magnetic fields can be generated without thermally overloading the exciting device.

According to another preferred embodiment, an intermediate element of a non-magnetic or non-magnetizable material (e.g., a washer or the like) is arranged between the magnetic or magnetizable element (for example, a fastening device in the form of a bolt) and a structure, such a component, which is to be connected therewith. This embodiment has the advantage that it measures directly the stress existing in the fastening device as a result of the fastening. The washer is optional and preferably consists of a non-ferromagnetic material.

In an alternative embodiment, a magnetic or magnetizable element is first arranged between a non-magnetic or non-magnetizable fastening device and a structure to be connected therewith. Advantageously, stress/strain conditions of a non-magnetic fastening device can therefore also be determined by measuring the mechanical stress that is transmitted by the fastening device to a preferably ferro-magnetic element (for example, a washer).

The method according to the invention is preferably used when measuring stress/strain conditions of fastening devices (such as screwed or inserted bolts, rivets, etc.). The method can be used in multiple manners, for example, in the maintenance of airplanes, helicopters, motor vehicles, etc.

Other objects, advantages and novel features of the present invention will become apparent from the following detailed description of the invention when considered in conjunction with the accompanying drawings.

DETAILED DESCRIPTION OF THE DRAWINGS

Figure 1:
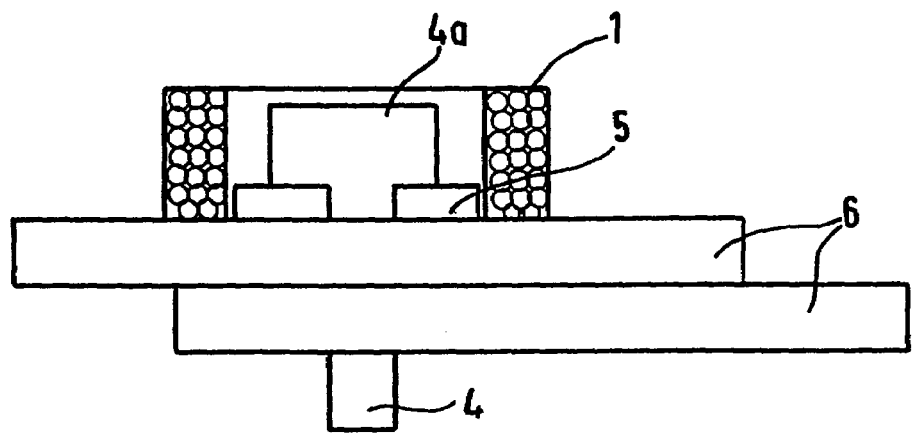
FIG. 1 is a schematic representation of a preferred embodiment for implementing the method according to the invention.

FIG. 1 shows a bolt 4 which is connected with a structure 6. As a rule, the bolt 4 is used for the fastening, fixing or holding of the structure which may comprise several components. The connection between the bolt 4 and the structure 6 may be screwed, riveted, inserted or the like. In the case of the screwed bolt illustrated in FIG. 1, a washer 5 is as a rule arranged between the head 4a of the bolt and the structure 6.

For determining the stress/strain condition of the bolt 4, in a first step, the coil, which has the reference number 1 in FIG. 1, is fitted over, onto or adjacent to the head 4a of the bolt. According to a preferred embodiment, the coil is used both for generating a magnetic field and for detecting the Barkhausen noise, as described in greater detail hereinafter. However, instead of the single coil 1, separate components can also be used: for example, a first coil for generating the magnetic field and a second coil which is used for detecting the Barkhausen noise. In the following discussion, reference will be made to the alternative embodiment, in which the exciting coil has the reference number 2 and the sensor coil 3, in each case by placing the corresponding components in parentheses.

Figure 2:
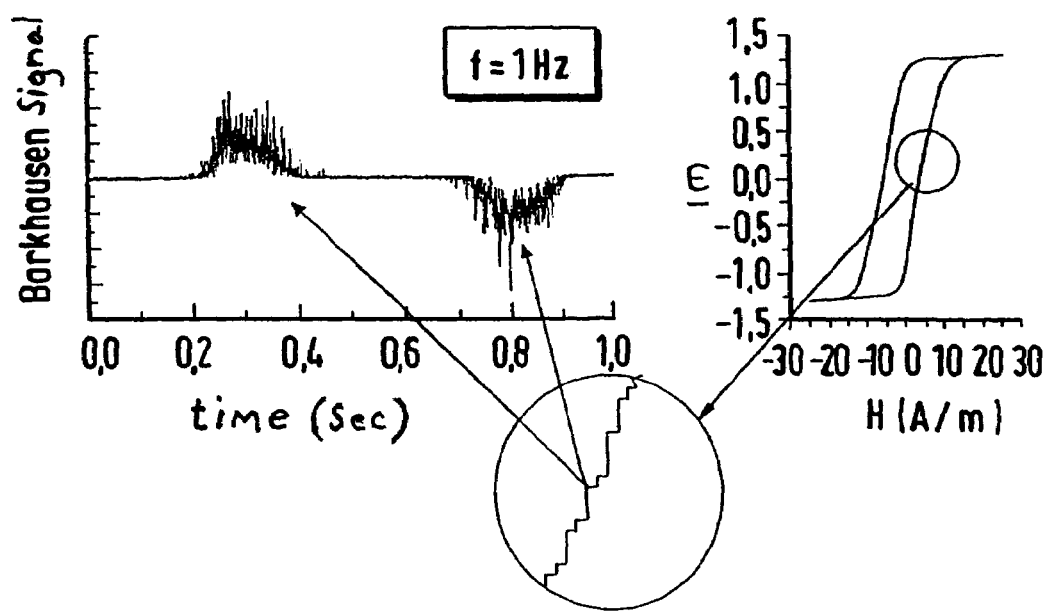
FIG. 2 is a view of representations of experimental measured values of the Barkhausen noise.

The coil 1 (or the exciting coil 2) is first used as a magnetizing coil and is excited by means of a magnetizing current for generating a magnetic field. If the bolt 4 is made of a ferromagnetic material, the magnetization field has the effect that the elementary magnets are aligned by the magnetic field of the coil 1 (or the exciting coil 2) through which the current flows. As known, the reversal of the elementary magnets is an erratic process (see FIG. 2) which results in a change of the magnetic flux, whereby a tension change is induced in the coil 1 (or in the sensing coil 3). The start of the reversal or alignment of the elementary magnets is a function of the magnetizing field intensity (or of the magnetizing current) and internal mechanical stress in the material. (A tensile stress applied to the bolt 4 opposes the alignment of the elementary magnets, or causes the elementary magnets to start to reverse once again, into their original alignment.) This reversal of the individual elementary magnets, in turn, generates a change of the magnetic flux, whereby currents (the so-called Barkhausen noise) are induced in the coil 1 (or in the sensing coil 3). Since the magnetic field intensity (or the magnetizing current) required to magnetize the bolt 4 is also a function of the internal mechanical stress, the stress/strain condition of the bolt 4 can be determined. In other words, a continuously rising magnetizing current generates a continuously rising magnetic field in the coil 1 (or the exciting coil 2), and the magnetizing current present at the start of the Barkhausen noise is a measurement of the tensile stress applied to the bolt 4.

As a rule, a pulsed magnetizing current is used to keep the thermal loading of the coil 1 (or of the exciting coil 2) as low as possible. Simultaneously, the start of the Barkhausen noise is monitored as a function of the magnetizing current through the coil 1 (or through the sensor coil 3). The measurement takes place inductively, the coil 1 in each case being set during the off-time of the pulses of the magnetizing current to receive the Barkhausen noise. For a precise determination of the stress/strain condition, comparative measurements, determined beforehand bolts (or rivets, etc.) made of the same material and of the same geometry, are used as a reference. The stress/strain condition is therefore determined by comparative measurements with previously determined measured values, for example, electronically filed in a table.

In addition, it should be noted that, during the measurement of the stress/strain condition of, for example, a ferromagnetic bolt, a washer made of a non-magnetic or non-magnetizable material should be used which, in the following, analogous to FIG. 1, has the reference number 5'.

The method according to the invention, can also be used to determine the stress/strain condition of a non-magnetic or non-magnetizable bolt 4'. In this case, a washer 5 made of a magnetic or magnetizable material is used, so that the stress transmitted from the bolt 4' to the washer 5 is correspondingly determined in the manner described above.

Figure 3:
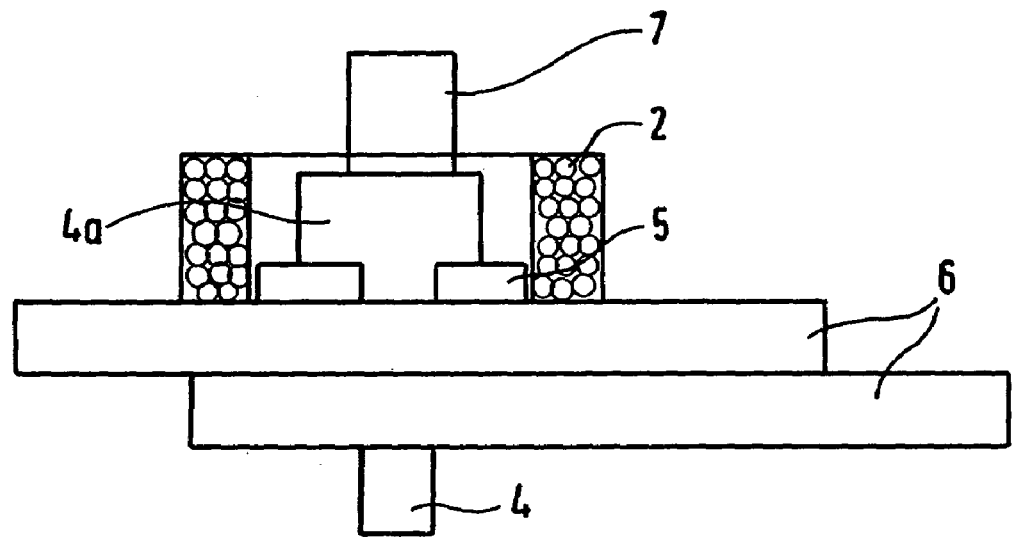
FIG. 3 is a schematic representation of a measuring arrangement as an alternative to FIG. 1.

As an alternative, instead of inductive determination by means of a sensing coil 3, the Barkhausen noise can be detected by means of an acoustic or interferometric detector 7, illustrated schematically in FIG. 3. The principle on which the invention is based is unchanged, only the Barkhausen noise is determined in a different fashion. The detector 7 may, for example, be a microphone or a piezoelement, to mention only a few examples.

Figure 4:
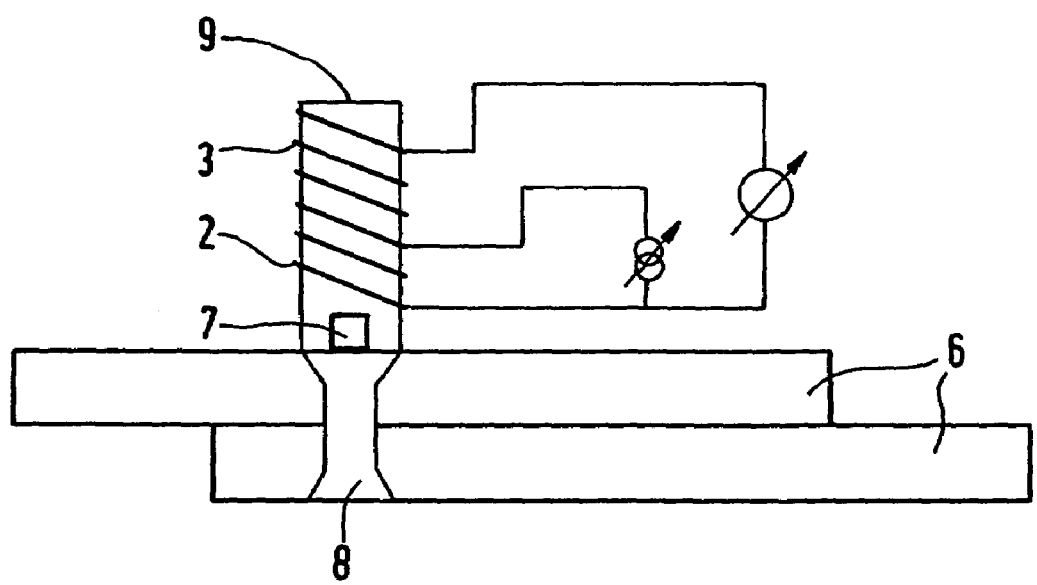
FIG. 4 is a schematic representation of an alternative measuring arrangement by means of a riveted connection.

FIG. 4 shows another alternative measuring arrangement on an example of a riveted connection. In FIG. 4, a rivet 8 is connected with the structure 6; and an exciting coil 2 and the sensing coil 3 are illustrated separately as wire-wound coils around a core 9. The exciting coil 2 is again acted upon by a variable magnetization, and the sensing coil 3 detects induced stress by flipping over the domains. Instead of the sensing coil 3, an acoustic or interferometric detector 7 can also be used here for the detection of the Barkhausen noise.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method of measuring stress/strain of magnetic or magnetizable elements by detecting Barkhausen noise, comprising:
    arranging an exciting/sensing device at least adjacent to said element;
    applying a continuously rising magnetizing current to the exciting device;
    detecting starting of Barkhausen noise by means of the sensing device;
    determining magnitude of the magnetizing current when the Barkhausen noise starts;
    comparing the determined magnitude of the magnetizing current when the Barkhausen noise starts with measured reference values to determine the stress/strain condition of the element; and
    outputting a signal representing the determined stress/strain condition of the element.

2. The method according to claim 1, wherein the exciting/sensing device is arranged in a manner in which it at least partially surrounds the magnetic or magnetizable element.

3. The method according claim 1, wherein an intermediate element made of a non-magnetized or non-magnetizable material is arranged between the magnetic or magnetizable element and a structure that is to be connected therewith.

4. The method according to claim 1, wherein:
    said continuously rising magnetizing current is pulsed; and the sensing device detects the Barkhausen noise during off-time of the pulses.

5. The method according to claim 3, wherein the magnetic or magnetizable element is arranged between a non-magnetic or non-magnetizable fastening element and a structure that is to be connected therewith, before the determination of its stress/strain condition.

6. The method according to claim 5, wherein the determined magnetizing current at the start of the Barkhausen noise is proportional to the internal stress of the element.

7. A method of measuring stress/strain in a magnetic or magnetizable item, comprising:

applying a continuously increasing magnetic field to said item;

detecting a time of commencement of Barkhausen noise generated in said item in response to said magnetic field;

determining strength of said magnetic field at said time of commencement of Barkhausen noise;

determining stress/strain in said item as a function of the determined strength of the magnetic field at said time of commencement of Barkhausen noise; and outputting a signal representing the determined stress/strain condition of the element.

8. The method according to claim 7, wherein said applying step comprises passing a continuously increasing magnetizing current through an exciting device situated in proximity to said item.

9. The method according to claim 8, wherein said step of determining strength of the magnetic field comprises measuring said magnetizing current at said time of commencement of Barkhausen noise.

10. The method according to claim 9, wherein said step of determining stress/strain in said item comprises comparing measured magnetizing current with measured reference values for said item.

* * * * *